United States Patent [19]
Inderbitzen et al.

[11] Patent Number: 5,713,854
[45] Date of Patent: Feb. 3, 1998

[54] METHOD AND APPARATUS FOR DILATATION CATHETERIZATION

[75] Inventors: Mark N. Inderbitzen, Miramar; Kirk L. Johnson, Miami Lakes, both of Fla.

[73] Assignee: Cordis Corporation, Miami Lakes, Fla.

[21] Appl. No.: 551,564

[22] Filed: Nov. 1, 1995

[51] Int. Cl.⁶ ............................................. A61M 31/00
[52] U.S. Cl. ......................... 604/53; 604/96; 604/102
[58] Field of Search ........................... 604/101, 102, 604/96, 166, 49, 53, 282, 280, 171, 264, 103, 104; 128/656–658; 606/192, 194

[56] References Cited

U.S. PATENT DOCUMENTS

| | | |
|---|---|---|
| 4,581,017 | 4/1986 | Sahota . |
| 4,752,286 | 6/1988 | Okada ............................. 604/96 |
| 4,762,129 | 8/1988 | Bonzel . |
| 4,771,777 | 9/1988 | Horzewski et al. ................. 128/344 |
| 4,944,745 | 7/1990 | Sogard et al. ..................... 606/194 |
| 5,040,548 | 8/1991 | Yock . |
| 5,049,132 | 9/1991 | Shaffer et al. . |
| 5,098,381 | 3/1992 | Schneider . |
| 5,284,473 | 2/1994 | Calabria ........................... 604/53 |
| 5,315,747 | 5/1994 | Solar . |
| 5,357,978 | 10/1994 | Turk . |
| 5,370,617 | 12/1994 | Sahota ............................. 604/102 |
| 5,383,853 | 1/1995 | Jung et al. . |
| 5,395,332 | 3/1995 | Ressemann et al. ................. 604/96 |

FOREIGN PATENT DOCUMENTS

| | | |
|---|---|---|
| 9217236 | 10/1992 | WIPO . |
| 9220397 | 11/1992 | WIPO . |
| 9411053 | 5/1994 | WIPO . |

*Primary Examiner*—Corrine M. McDermott
*Assistant Examiner*—Cris L. Rodriguez
*Attorney, Agent, or Firm*—Watts, Hoffmann, Fisher & Heinke, Co., L.P.A.

[57] ABSTRACT

Apparatus and method is disclosed for facilitating balloon catheter exchange in angioplasty procedures. A guide catheter allows the balloon catheter to be inserted into the subject to a region near a treatment region within the vascular system. A fluid source is provided for selectively inflating the balloon. A passageway in the catheter body that extends through the catheter balloon opens into the blood vessel via a sideport. A guidewire passageway extends through a distal most part of the catheter body to allow a guidewire to be inserted into the sideport and routed out the catheter body through a distal opening.

6 Claims, 3 Drawing Sheets

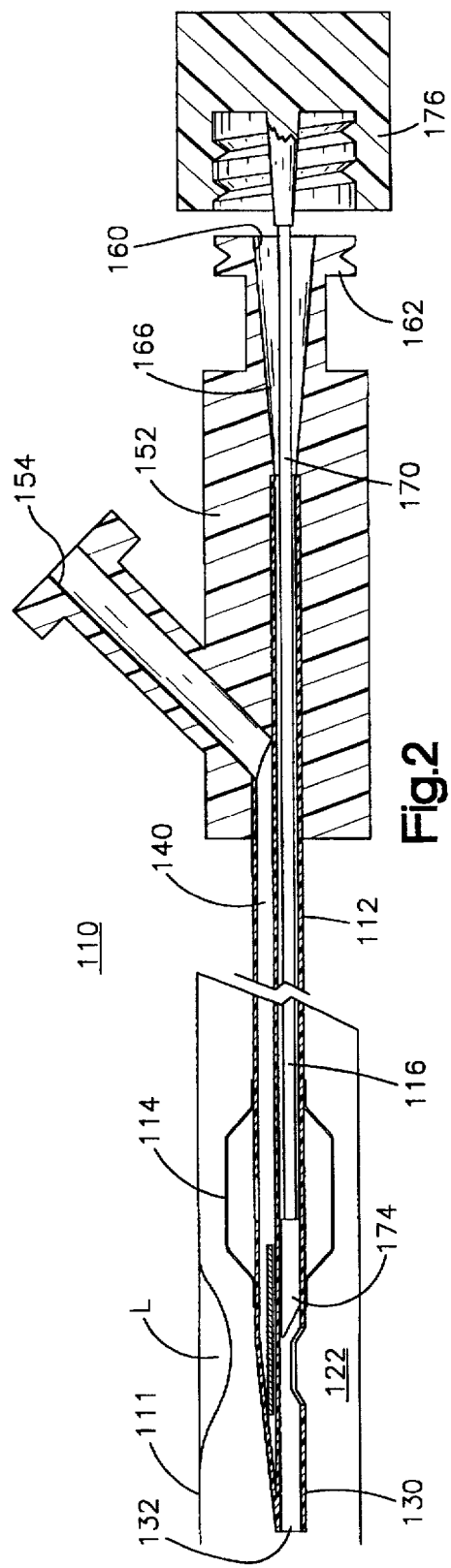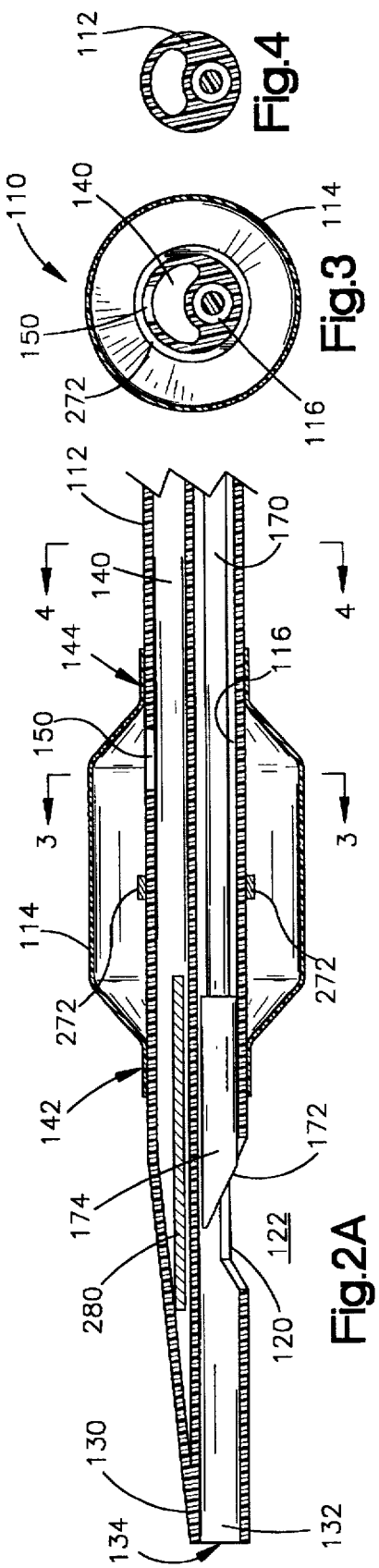

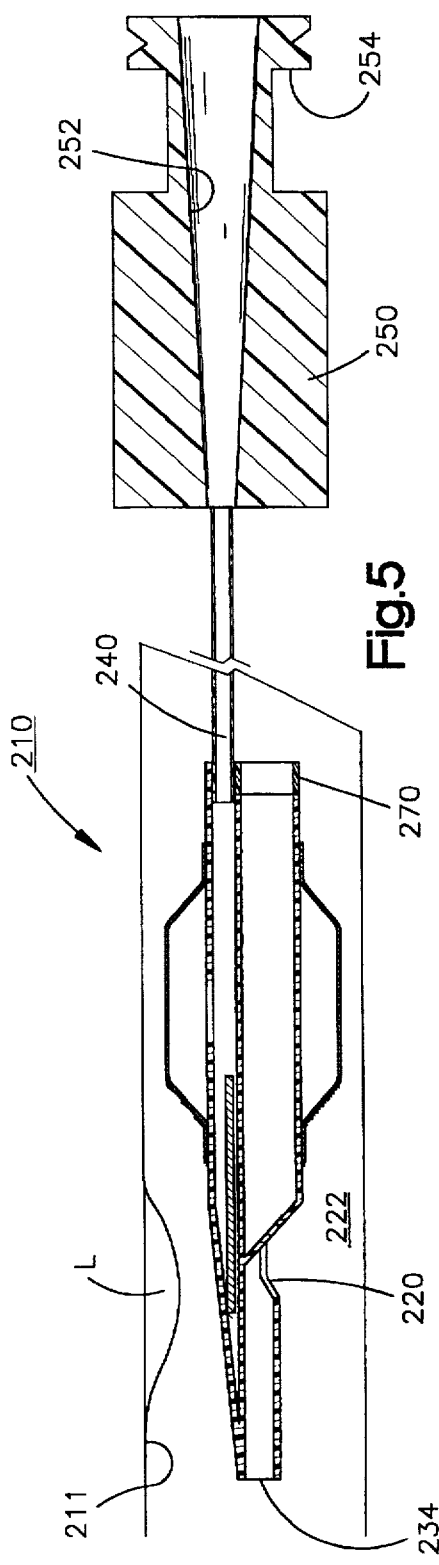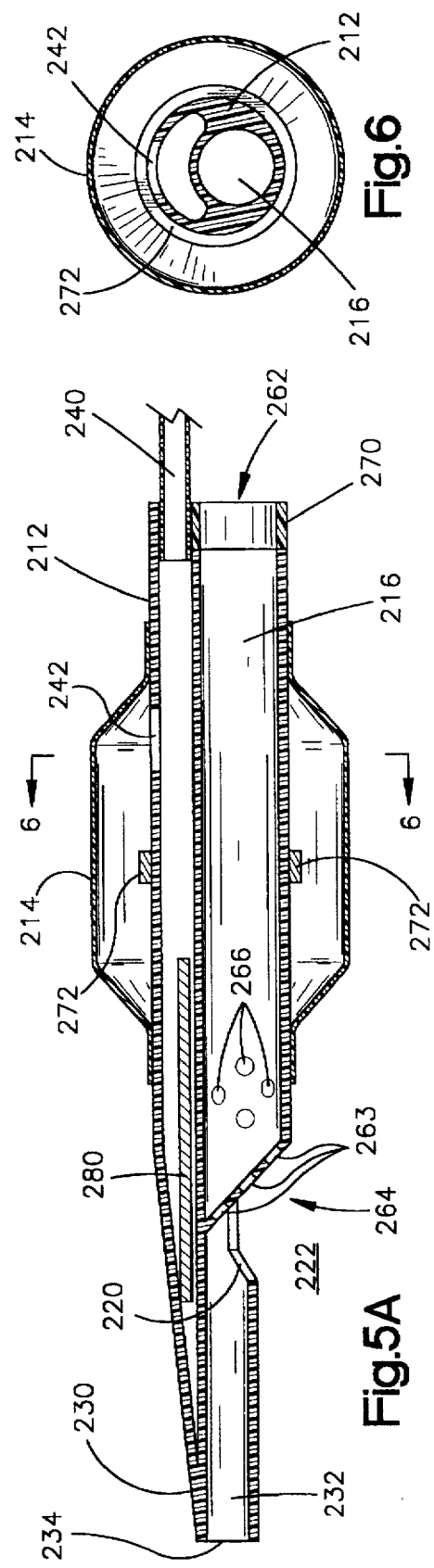

5,713,854

METHOD AND APPARATUS FOR DILATATION CATHETERIZATION

TECHNICAL FIELD

This invention relates generally to the field of catheterization, and more specifically to new apparatus and method for facilitating balloon exchange during dilatation procedures such as angioplasty.

BACKGROUND ART

Catheterization procedures are well known for diagnosis and therapy of lesions in the cardiovascular system. One such procedure is angioplasty which reduces the damaging effects of vascular plaque blockage or constriction in blood vessels.

In an angioplasty procedure, an expandable balloon is introduced into the patient's arterial system and advanced until it is positioned in the region of the blockage or constriction. Once so positioned, the balloon is expanded by filling it with a liquid. In successful procedures, the expandable balloon presses outwardly against the walls of the artery and expands the artery to a degree to which the artery is either partially or totally re-opened to blood flow.

A typical angioplasty procedure, and components used in practicing the procedure, are now described.

Prior to initiating the angioplasty procedure, a guiding catheter is placed typically via the femoral artery into the aorta and its tip is engaged into the coronary arteries which branch from the aorta. This entrance into the coronary artery is called the ostium. Once placed, the guiding catheter acts as a conduit to access the coronary arteries with a balloon guidewire and balloon catheter. The guiding catheter is a portion of plastic tubing having a length of about 95 centimeters, an inside diameter of about 0.08 inches, and an outside diameter of about 2.5 millimeters.

The physician positions a balloon catheter within the patient with the aid of a guidewire. The guidewire is a piece of elongated wire, approximately 175 centimeters in length, and about 0.010–0.018 inches in diameter. The distal tip of the guidewire can be shaped to form a "J" configuration. This "J" shape allows the physician to steer the wire by twisting the proximal extremity of the guidewire while advancing or retracting the guidewire.

The balloon catheter is an elongated flexible member having a balloon located near its distal end. In a so called "Over-the-Wire" catheter system one longitudinal opening through the catheter defines a sleeve through which the balloon guidewire can be passed. A second longitudinal passage in the catheter defines a conduit communicating with the interior of the balloon and through which inflation fluid can be injected to inflate the balloon.

Among the types of balloon catheters is one of a type in which the two longitudinal passages are generally side by side and parallel. In another type of balloon catheter, the two longitudinal passages are co-axial. In this latter type, the balloon guidewire is passed down the inner passage and the inflation fluid is injected into the balloon via the outer passage.

Balloon catheters, as well as associated apparatus and method for use in angioplasty, are described in U.S. Pat. No. 5,040,548, issued on Aug. 20, 1991, to Yock, and U.S. Pat. No. 4,762,129, issued on Aug. 8, 1988. Each of these issued U.S. patents is hereby expressly incorporated by reference.

Using the over-the-wire insertion technique, the physician passes the balloon guidewire through the guidewire passage in the balloon catheter, leaving a portion of the balloon guidewire extending from the distal end of the balloon catheter and also a portion extending from its proximal end.

This assembly is then inserted into the proximal end of the guiding catheter, distal end first. The assembly is inserted until the balloon catheter which is attached near the distal end of the balloon catheter is near the distal end of the guiding catheter. At this point, the physician, while maintaining the balloon catheter stationary, pushes on the balloon guidewire to advance it outwardly from the distal end of the guiding catheter.

The balloon guidewire can be steered by appropriate twisting movement by the physician. The physician steers the guidewire into the chosen one of the coronary arteries, and advances it until it reaches a location of constriction which the physician desires to re-open. Carefully, the physician eases the guidewire through the region of restriction until a portion of the guidewire is on the opposite side of the constriction, relative to the guiding catheter.

With the balloon guidewire held stationary, the physician then advances the balloon catheter. The distal end of the balloon catheter, as it is advanced, will, of course, follow the balloon guidewire which is already in place.

The physician continues to advance the balloon until it is located in the region of constriction of the artery. With the balloon and its associated catheter held stationary, inflation fluid is injected into the conduit which communicates with the balloon, causing it to inflate. Inflation of the balloon expands the walls of the artery in the region of constriction and, in successful procedures, re-opens the artery to sufficient blood flow.

Arteries vary in size, and therefore balloon catheters having balloons of different sizes are provided for the physician's selection. These balloons, when inflated, range from about 1.5 millimeters to about 4 millimeters in diameter.

Sometimes, it is necessary for the physician to use more than one balloon to open an artery. Sometimes, the chosen balloon is too large to be advanced into the constricted area. In other instances, the first chosen balloon size, even when inflated, is not large enough to open the constricted area to the degree desired. In such cases, it is necessary to exchange one balloon for another during the same angioplasty procedure.

In order to accomplish this exchange, the guidewire is left in place, and the balloon catheter is withdrawn entirely from the guiding catheter until it is completely disengaged from the guidewire. A new balloon catheter, having a different sized balloon, is then re-inserted over the guidewire and advanced back to the location of the constricted area, where it is used to effect the desired result.

Once the guidewire has been inserted through the constricted area, it is desirable to leave the guidewire in place for the entire angioplasty procedure; even during exchanges of balloons. The reason for this is that, when a foreign object, such as the guidewire, is introduced into an artery, the artery walls sometimes go into spasm, and constrict generally along a substantial portion of its length. If the artery tends to contract in this way, removal of the guidewire while the artery is so contracted will sometimes render it virtually impossible to re-insert the guidewire through the contracted artery.

Additional prior art patents relating to balloon catheters are U.S. Pat. Nos. 4,762,129 to Bonzel, 5,098,381 to Schneider, 5,049,132 to Shaffer et al, and 5,315,747 to Solar and published PCT applications WO 92/17236 to Tartaglino et al and WO 92/20397 to Jung.

The Bonzel '381 patent concerns a so-called "rapid exchange" guidewire arrangement. Using such an arrangement the guidewire can be inserted and properly positioned before the catheter is inserted into the guide catheter.

It is a general object of the present invention to provide apparatus and method for facilitating introduction and exchange of balloons in angioplasty procedures.

DESCRIPTION OF THE INVENTION

The apparatus and method of the present invention concern a catheter system that includes a balloon catheter that can be positioned relative to a treatment region of a subject's vascular system. The system also includes a tubular guiding catheter sized for insertion into the vascular system of a subject to help position the balloon catheter. An elongated guidewire longer than the tubular guiding catheter is pushed through the balloon catheter and is used in positioning the balloon catheter after the balloon is pushed through the guide catheter.

A preferred balloon catheter constructed in accordance with the present invention includes an elongated catheter body and an inflatable catheter balloon coupled to the elongated catheter body near a distal end of the catheter body. The catheter body defines a conduit for transmitting fluid from outside the subject through the catheter body into an interior of the catheter balloon once the balloon is positioned relative to the treatment region. The catheter body also defines a longitudinal passageway that extends through the catheter balloon to a sideport in the catheter body where the longitudinal passageway opens outwardly into the blood vessel at a location distal to the balloon. A catheter body section distal of the balloon defines a guidewire passage that opens into the blood vessel via the sideport and extends through the body section to a distal opening spaced from the sideport. A source of inflation fluid is coupled to the catheter body for injecting fluid through the conduit to inflate the catheter balloon.

In accordance with two different disclosed embodiments of the invention the catheter balloon is a dilation balloon used to compress regions of the inner wall linings of a blood vessel. In accordance with one of these two embodiments the catheter is a perfusion catheter which allows blood to flow through the catheter while the balloon is inflated and pressing against the inner lining of a blood vessel.

The structure of the disclosed balloon catheter enhances an ability to position the balloon relative the treatment region of the subject. This and other objects, advantages and features of alternate embodiments of the invention are described in conjunction with the accompanying drawings.

BRIEF DESCRIPTION OF THE DRAWINGS

FIG. 2 is a sectional view of a catheter constructed in accordance with the present invention;

FIG. 2A is an enlarged sectional view of the FIG. 2 catheter;

FIG. 3 is a view of the catheter as seen from the plane 3—3 of FIG. 2A;

FIG. 4 is a view of the catheter as seen from the plane 4—4 of FIG. 2A;

FIG. 5 is a sectional view of an alternate catheter constructed in accordance with the present invention;

FIG. 5A is an enlarged sectional view of the FIG. 5 catheter; and

FIG. 6 is a sectional view as seen from the plane 6—6 of FIG. 5A.

BEST MODE FOR CARRYING OUT THE INVENTION

Figure 1:
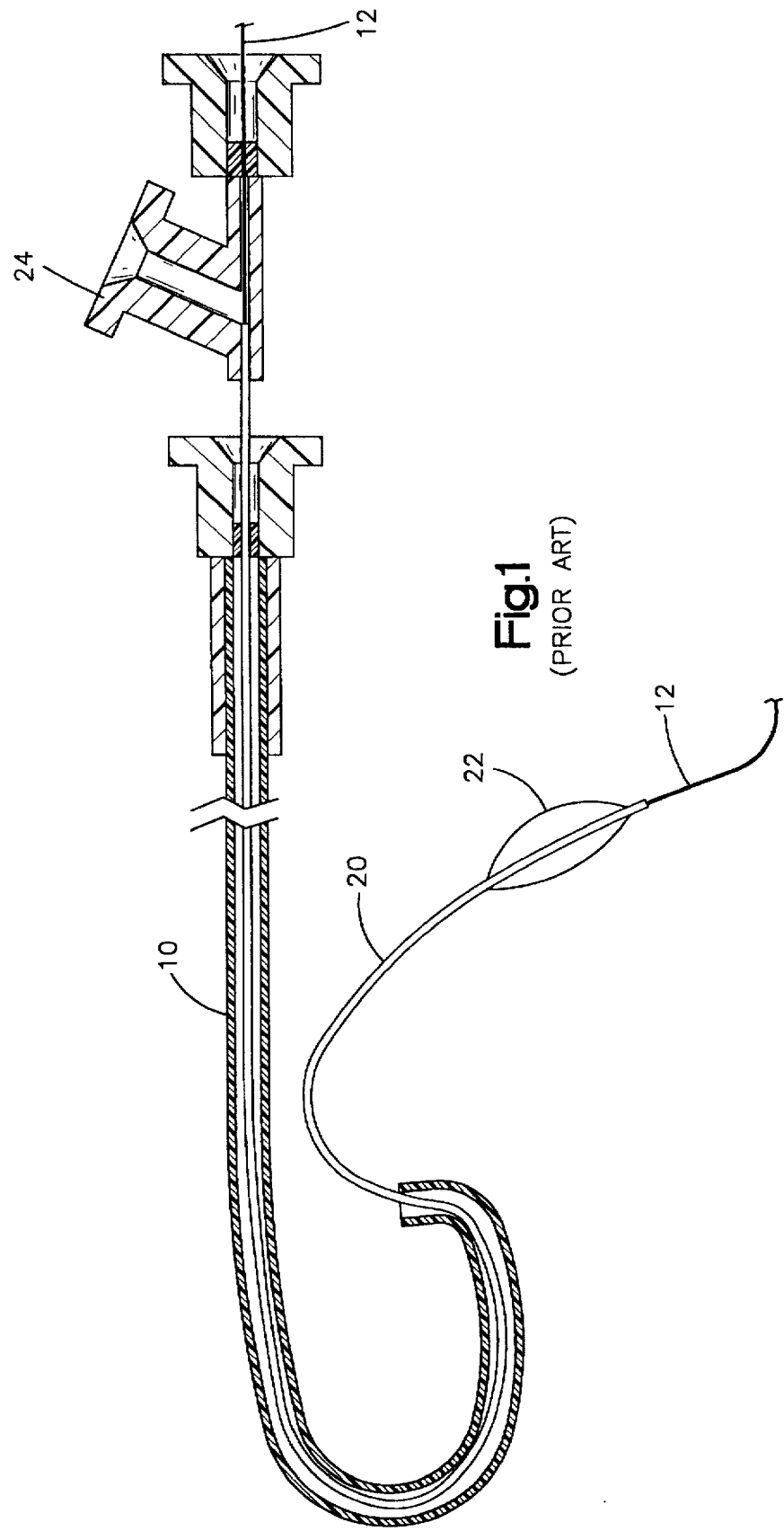
FIG. 1 is an elevational view, partly in cross-section, illustrating a prior art balloon catheter system.

FIG. 1 shows the relevant portions of a system for positioning a balloon catheter in relation to a treatment region. A guiding catheter 10 that has been positioned within a patient subject's arterial system as described above.

A balloon guidewire 12 is also illustrated. The balloon guidewire 12 extends outwardly from a distal end of a balloon catheter 20 at a treatment region of the subject.

The balloon catheter 20 is illustrated with the balloon guidewire 12 passing through a longitudinal passage extending through the balloon catheter. The balloon catheter 20 of FIG. 1 is of the type wherein the longitudinal passage for accommodating the balloon guidewire is central and surrounded by a second co-axial passage for transmitting inflation fluid to a balloon 22.

The catheter balloon 22 is inflated by the injection of inflation fluid into an inflation port 24 to expand outwardly to contact and impose outward pressure on the inner walls of a blood vessel in which the balloon has been positioned. Preferably, the inflation fluid is a known type of radiopaque liquid. The radiopaque nature of the liquid permits the configuration of the balloon 22 to be imaged by known apparatus and viewed by the physician on a continuous real time basis. The balloon catheter is made of an extrusion of known relatively flexible plastic, such as nylon. The same is true of the guiding catheter.

It is to be understood that, as an alternative to the balloon catheter construction shown in FIG. 1, the balloon catheter may be of another known configuration in which the longitudinal passages extending through the balloon catheter are not co-axial. In such an alternative embodiment, the longitudinal passages through the balloon catheter are side by side and substantially parallel.

By pushing on the proximal end of the balloon catheter an attending physician can advance the balloon catheter and its associated balloon 22 all the way through the guiding catheter 10 and out a distal end of the guiding catheter, from which the balloon catheter and balloon will track the balloon guidewire until the balloon reaches a treatment region.

When it is desired to inflate the balloon 22, inflation fluid is forced under pressure into the infusion port 24 of the balloon catheter by known means, such as a syringe.

FIG. 1 illustrates a situation in which the physician has advanced the balloon catheter to the point at which the balloon 22 attached to the end of the balloon catheter, has exited the distal end of the guiding catheter 10. It is to be understood that the balloon 22 is located within an artery of the patient, which artery is not shown. The balloon guidewire 12 is pre-located within the patient's artery and extends past the area of blockage or constriction.

FIGS. 2, 2A, 3 and 4 depict a balloon catheter 110 constructed in accordance with one embodiment of the invention. The catheter 110 is placed within a subject blood vessel 111 for treatment of a lesion L within the vessel by applying a force of compression against the lesion L.

The catheter 110 includes an elongated catheter body 112 and an inflatable catheter balloon 114 coupled to the elongated catheter body 112 near a distal end of said catheter body. The catheter body defines a longitudinal passageway 116 that extends through the catheter balloon to a sideport 120 in the catheter body that opens outwardly from a sidewall of the catheter body into a region 122 within a blood vessel adjacent the sideport 120.

The catheter body also has a body section 130 distal of the balloon 114 having a guidewire passage 132 that opens into the region 122 within the blood vessel near the sideport 120. The guidewire passage 132 also extends through the body section 130 to a distal opening 134 spaced from the sideport 120. The catheter body 112 also has a conduit or passageway 140 for transmitting fluid from outside the subject through the catheter body into an interior of the catheter balloon once the balloon 114 is properly positioned relative to the lesion L.

The catheter shown in FIG. 2 includes a dilatation balloon 114. Such a balloon is fused around the circumferential extent of the catheter body 112 at two spaced apart locations 142, 144 by heat fusing techniques known in the art. Midway between the spaced locations 142, 144 the catheter body includes an opening 150 that opens outwardly from the passageway 140 into the interior of the balloon 114. As seen in FIG. 2 the passageway 140 extends outside the subject through the catheter body to a fitting 152 having a side port 154 for injecting fluid into the catheter body through the passageway 140. Once the balloon has been positioned in bridging relation with the lesion L, the fluid is forced into the catheter to inflate the balloon and compress the lesion.

The catheter can be positioned using either the "over-the-wire" or the "rapid exchange" technique where the guidewire does not pass through the proximal portion of the catheter body 112. In an over the wire procedure the guidewire enters the fitting 152 by a proximal port 160 having a threaded connector portion 162. The guidewire extends through a passageway 166 in the fitting 152 to the passageway 116 in the catheter body. The guidewire 12 extends through the passageway 116, past the sideport 120, through the distal body portion passageway 132 and out the distal opening 134.

When used in the "rapid exchange" mode of catheter placement, the guidewire passes through the sideport 120. The guidewire is first pushed through an appropriately positioned guide catheter until the distal end of the guidewire exits the guide catheter. The guidewire is then guided by the physician into and through the region of an obstruction. Outside the subject the physician then pushes the distal opening 134 of the catheter over the guidewire's proximal end and pushes until the guidewire exits the distal portion of the catheter body through the sideport 120. Since the guidewire is already properly positioned relative to the lesion L, the catheter can be pushed along the guidewire to exit the guide catheter and the balloon brought into bridging relation with the lesion L.

Using this alternate guidewire configuration the catheter 110 can also be withdrawn from the guide catheter 10 without disturbing the position of the guidewire 12 and a different catheter routed over the guidewire to the treatment region. In this embodiment the body passageway 116 is used to insert a stiffening mandrel 170. The stiffening mandrel 170 has a ramp 172 at an enlarged distal end 174 that closes off the passageway 116 to prevent the guidewire from entering the passageway 116 as the catheter is pushed over the proximal end of the guidewire. The pushability and flexibility of the catheter can be controlled by control of the stiffness of the stiffening mandrel 170. A leur fitting 176 is attached to the proximal end of the mandrel. With the leur fitting 176 attached to the threaded connector portion 162 of the fitting 152 the mandrel 170 is positioned with respect to the catheter to close off the port 120.

ALTERNATE EMBODIMENT

FIGS. 5, 5A and 6 illustrate an alternate embodiment of a catheter 210 constructed in accordance with the invention. The catheter 210 includes an elongated catheter body 212 and an inflatable catheter balloon 214 coupled to the elongated catheter body 212 near a distal end of the catheter body. The catheter body defines a longitudinal passageway 216 that extends through the catheter balloon to a sideport 220 in the catheter body that opens outwardly into a region 222 within a blood vessel 211 adjacent the sideport 220. The passageway is most preferably constructed from a tube of plastic material used to construct catheter bodies such as nylon.

The catheter body also has a body section 230 distal of the balloon 214 having a guidewire passage 232 that opens into the region 222 within the blood vessel near the sideport 220. The guidewire passage 232 also extends through the body section 230 to a distal opening 234 spaced from the sideport. The catheter body also defines a conduit 240 for transmitting fluid from outside the subject through the catheter body 212 into an interior of the catheter balloon once the balloon 214 is positioned relative to a treatment region such as in bridging relation to a lesion L within the blood vessel. In the region of the catheter body bounded by the balloon the body has an opening 242 that fills the balloon 214 with fluid that travels the length of the catheter through the passage 240.

The catheter depicted in FIGS. 5 and 5A is a perfusion catheter. A guidewire is inserted into the opening 234, through the passageway 232 and out the sideport 220. The balloon 214 is positioned within the subject blood vessel and then a fluid is injected through the passageway 240 from a fitting 250 having a center passage 252 bound by a threaded coupling 254 at the extreme proximal end of the catheter 210.

In the embodiment illustrated in FIG. 5A the passageway 216 that extends through the balloon allows blood to flow into an opening 262 in a the catheter body, flow through the generally cylindrical passageway 216 and exit the catheter body. Plural openings 263 in a ramp portion 264 of the body allow blood that enters the passage 216 to exit from the catheter body at a location distal to the balloon. Additional side openings 266 that extend through the walls of the catheter body also allow blood to exit the catheter at a point distal to the balloon 214. The openings 263 in the ramp are small enough to prevent the guidewire from entering the passageway 216 as the catheter is pushed over the guidewire.

The tube that defines the passageway 216 supports a short annular extension 270 that is fused to the catheter body. The extension is constructed from a low durometer radiopaque polymer that does not damage the blood vessel when the catheter is withdrawn back into the guide catheter. To aid the physician in keeping track of the position of the balloon either embodiment of the invention can include a radiopaque marker. Such a marker 272 is schematically depicted in FIG. 5A.

Each of the embodiments described above has a cutout portion that defines a side port for insertion of a guidewire at a point distal to the balloon. But for use of a stiffening rod 280 at the region of the sideports each of the catheters would be weakened and made too flexible at the region of the side port. The stiffening rod 280 is attached to the body of the catheter by placing the rod 280 in the passageway 140 for the embodiment of FIGS. 2, 2A, 3, and 4 or in the passageway 240 for the embodiment of FIGS. 5, 5A, and 6 and fusing the rod to the catheter body when the distal end of the catheter is fused into a tapered distal tip.

While the present invention is described above in considerable particularity, it is to be understand that those of ordinary skill in the art may be able to make certain additions or modifications to, or deletions from, the specific embodiments described herein, without departing from the spirit or the scope of the invention, as set forth in the appended claims.

We claim:

1. A method for placing a catheter within a subject blood vessel comprising the steps of:
    a) providing a balloon catheter having an inflatable balloon at a distal location and having a catheter body that defines a guidewire passage extending through the catheter body from a distal opening at the balloon catheter's distal tip to a sideport that opens outwardly from a sidewall of the catheter body into the blood vessel at a catheter body location between the balloon and the distal opening;
    b) inserting a guide catheter into a subject and positioning the guide catheter relative a treatment region of a subject blood vessel;
    c) inserting a flexible guidewire into a proximal end of the guide catheter and pushing the guidewire through the guide catheter body and out the distal end of the guide catheter to bring the guidewire into position relative to the treatment region;
    d) pushing the distal opening of the balloon catheter over a proximal end of the guidewire and routing the proximal end of the guidewire out the sideport and then pushing the balloon catheter into the subject along the guidewire to position the balloon at a treatment region within a subject vessel; and
    e) inflating the balloon to bring outer wall portions of the balloon into contact with inner wall portions of the subject blood vessel,
    wherein the balloon catheter further defines an elongated passageway extending from a proximal end of the catheter to the sideport that allows over-the-wire insertion of the balloon catheter into the subject and comprising the additional step of inserting a stiffening mandrel into the elongated passageway until an end of the passageway is blocked by the mandrel to avoid insertion of the proximal end of the guidewire into the elongated passageway.

2. A catheter for placement within a subject comprising:
    an elongated catheter body and an inflatable catheter balloon coupled to the elongated catheter body for placement within the subject relative to a treatment region of a vascular system of the subject,
    the catheter body defining an inflation lumen for transmitting fluid from outside the subject through the catheter body into an interior of the catheter balloon once the catheter balloon is positioned relative to the treatment region,
    the catheter body having a distal end and defining a distal opening near the distal end, the catheter body also defining a longitudinal passageway that extends from outside the subject through the catheter balloon to the distal opening near the distal end of the catheter body,
    the catheter body having a location spaced from the distal opening and distal to the catheter balloon, the catheter body further defining a sideport that opens outwardly from the longitudinal passageway at the location spaced from the distal opening and distal to the catheter balloon such that the catheter body defines a guidewire passage through the distal opening into the longitudinal passageway and out of the longitudinal passageway through the sideport for insertion of a guidewire; and
    a removable elongated stiffening mandrel adapted to extend from outside the subject and through the longitudinal passageway to a position proximal to the sideport such that the mandrel prevents further insertion of the guidewire into the longitudinal passageway proximal to the sideport thereby causing the inserted guidewire to exit through the sideport.

3. The catheter of claim 2, wherein the catheter body is adapted for over-the-wire insertion of the catheter body into the subject by insertion of a guidewire through the distal opening and into the longitudinal passageway when the mandrel is removed from the longitudinal passageway.

4. The catheter of claim 2, additionally comprising a stiffening rod connected to the catheter body that adds a stiffness to the catheter at the sideport.

5. The catheter of claim 2, further comprising a connector attached to the catheter body outside the subject and additionally comprising a fitting attached to a proximal end of the stiffening mandrel for positioning the mandrel in the longitudinal passageway as the fitting abuts the connector.

6. The catheter of claim 2, in combination with:
    a guiding catheter for insertion into the vascular system of the subject, the guidewire for insertion into the guiding catheter to a position relative to the treatment region of the subject and for insertion through the guidewire passage of the catheter body to guide the catheter body to a position relative to the treatment region; and
    a source of inflation fluid that can be coupled to the catheter body for injecting fluid through the inflation lumen in the catheter body to inflate the catheter balloon.

* * * * *